United States Patent
Svochak et al.

(10) Patent No.: US 8,696,117 B2
(45) Date of Patent: Apr. 15, 2014

(54) FITTING A CONTACT LENS

(75) Inventors: Jan Barry Svochak, Hurst, TX (US); Brandon Jan Svochak, Euless, TX (US)

(73) Assignee: Truform Optics, Euless, TX (US)

( * ) Notice: Subject to any disclaimer, the term of this patent is extended or adjusted under 35 U.S.C. 154(b) by 222 days.

(21) Appl. No.: 12/881,741

(22) Filed: Sep. 14, 2010

(65) Prior Publication Data
US 2012/0062844 A1    Mar. 15, 2012

(51) Int. Cl.
*G02C 7/04* (2006.01)

(52) U.S. Cl.
CPC . *G02C 7/047* (2013.01); *G02C 7/04* (2013.01)
USPC ............ 351/159.74; 351/159.8; 351/247

(58) Field of Classification Search
CPC ........... G02C 7/047; G02C 7/04; A61B 3/107
USPC .............. 351/247, 177, 159.73, 159.74, 159.8
See application file for complete search history.

(56) References Cited

U.S. PATENT DOCUMENTS

| | | | |
|---|---|---|---|
| 4,787,732 A * | 11/1988 | Siviglia | 351/160 R |
| 4,798,460 A | 1/1989 | Buffington et al. | |
| 4,801,198 A | 1/1989 | Heacock et al. | |
| 4,838,682 A | 6/1989 | Portnoy | |
| 4,863,260 A | 9/1989 | Gersten et al. | |
| 5,293,533 A | 3/1994 | Klyce | |
| 5,686,981 A * | 11/1997 | Anan et al. | 351/212 |
| 5,707,614 A | 1/1998 | Joshi et al. | |
| 5,717,781 A * | 2/1998 | Ebel et al. | 382/141 |
| 6,076,930 A | 6/2000 | Malchow et al. | |
| 6,438,398 B1 | 8/2002 | Pflugfelder et al. | |
| 6,648,473 B2 | 11/2003 | Della Vecchia et al. | |
| 7,249,849 B2 | 7/2007 | Marmo et al. | |
| 7,281,801 B2 | 10/2007 | Wang | |
| 7,384,143 B2 | 6/2008 | Hall et al. | |
| 7,654,957 B2 | 2/2010 | Abreu | |
| 7,758,190 B2 | 7/2010 | Korb et al. | |
| 7,771,353 B2 | 8/2010 | Luce | |
| 7,901,077 B2 * | 3/2011 | Dai et al. | 351/247 |
| 7,990,531 B2 * | 8/2011 | Clements et al. | 356/239.2 |

OTHER PUBLICATIONS

Hersh, Peter S., Ramakrishna Ratnakaram, Donald Hersh, and Kristen Fry. "Diagnostic Use of a Rigid Contact Lens to Show Corneal Topography Abnormalities After Laser Refractive Surgery." Journal of Cataract Refractive Surgery 25 (2002): 2054-2057. Print.*
Federal Register vol. 76, No. 27 pp. 7162-7175.*

* cited by examiner

*Primary Examiner* — Zachary Wilkes
(74) *Attorney, Agent, or Firm* — Yee & Associates, P.C.

(57) ABSTRACT

The different illustrative embodiments provide a method, computer system, and computer program product to fit a lens. The method comprises obtaining an image of the lens. The method also comprises identifying an edge of a lens on an eye in the image. The method also comprises associating a number of zones with the image of the lens based on the edge of the lens. The method also comprises identifying the value for each zone in the number of zones based on intensities within the lens. The method also comprises designing a new lens based on the value to reach a desired value.

18 Claims, 9 Drawing Sheets

|  | PWR | BC | D1 lens | PC1 | D2 lens | PC2 | D3 lens | PC3 | D4 lens | PC4 | D5 lens |
|---|---|---|---|---|---|---|---|---|---|---|---|
| LENS | -6.25 | 6.20 | 8.00 | 6.40 | 10.0 | 7.50 | 11.0 | 9.20 | 13.0 | 11.75 | 15.00 |
|  | Cclear | Clear @ D1 | D1 fit | Clear @ D2 | D2 fit | Clear @ D3 | D3 fit | Clear @ D4 | D4 fit | Clear @ D5 | D5 fit |
| FIT | 0.000 | 0.000 | 8.00 | 0.000 | 10.0 | 0.100 | 11.0 | 0.050 | 13.0 | 0.020 | 15.00 |
|  | Cclear | Clear @ D1 | D1 | Clear @ D2 | D2 | Clear @ D3 | D3 | Clear @ D4 | D4 | 1.00 | D5 |
| REDESIGN | 0.050 | 0.050 | 8.00 | 0.050 | 10.0 | 0.050 | 11.0 | 0.000 | 13.0 | 0.100 | 15.00 |

FITTING A CONTACT LENS

BACKGROUND OF THE INVENTION

1. Field of the Invention

The present invention relates generally to designing and manufacturing contact lens eyewear and more specifically to a method for fitting contact lenses.

2. Description of the Related Art

Optical enhancement devices and refractive surgery are two techniques used to correct vision. One reason to correct vision is due to myopia, also referred to as nearsightedness. Refractive surgery may include radial keratotomy and photorefractive keratotomy. Optical enhancement devices may include contact lenses and glasses. Contact lenses are prescribed to correct refractive errors in vision. Optical enhancement devices may still be used after refractive surgery if there is still some nearsightedness. Contact lenses include soft contact lenses and rigid gas permeable contact lenses. Rigid gas permeable contact lenses are examples of hard contact lenses.

Rigid gas permeable lenses may be more durable than soft contacts and better for correcting astigmatism than soft contacts. Further, the shape of the rigid gas permeable lens may be modified as opposed to soft contacts, and require less maintenance than soft contacts. One method currently used to fit rigid gas permeable lenses involves weeks of trying various shapes for the rigid gas permeable lens using experimental fitting techniques.

To fit rigid gas permeable lenses, the optometrist or other person performing the fitting may apply fluorescein dye drops to the eyes of the patient to reveal the amount of clearance, or distance, between the rigid gas permeable lens and the corneal surface. Fluorescein is a bright orange dye that fluoresces with a color that is lime green in the presence of cobalt blue light. In the fitting process, as more clearance is present between the rigid gas permeable lens and the cornea, more dye accumulates in the clearance. This increase in accumulation is indicated by a fuller green fluorescence of the dye. The fluorescein test is considered reliable but is not usable with the popular soft contact lenses because the material used in soft contact lenses. These materials often include hydrogel, which absorbs the fluorescein dye. As a result the soft contact lens becomes stained.

A fluorescein pattern showing the rigid gas permeable lens with even clearance between the rigid gas permeable lens and the eye along the cornea of the eye with only slight tear pooling between the lens and cornea may be considered a good fit. Tear pooling is indicated by the amount of fluorescein that accumulates.

During a fitting, after the optometrist has applied the fluorescein drops, an evaluation of the tear pooling indicates what type of correction to the rigid gas permeable lens may be made, if a correction is made. Different types of tear pooling patterns may indicate different correctional steps. Correctional steps on a new design of the rigid gas permeable lens may be made, for example, by making changes to the base curve radius, overall diameter, optical zone diameter, secondary curve radius, peripheral curve radius, and/or center thickness.

Current methods for fitting rigid gas permeable lenses often involve many sessions to perform fittings with the optometrist evaluating the fluorescein and tear pooling to make correctional steps in each session. The correctional steps are used to create a new design for the rigid gas permeable lens. After each new design, another session for a fitting may be performed and that session may result in yet another new design. It would be useful to provide a method of fitting rigid gas permeable lenses which decreases the number of fitting sessions.

The method of fitting using trial lenses is a long and laborious process, and can be very expensive if the rigid gas permeable lenses are difficult to manufacture. Additionally, arriving at a precise fit can require many weeks or months using many different trial rigid gas permeable lenses. During this time the patient does not have use of the desired or needed rigid gas permeable lens.

Accordingly, it would be advantageous to have a method and apparatus, which takes into account one or more of the issues discussed above as well as possibly other issues.

BRIEF SUMMARY OF THE INVENTION

The illustrative embodiments provide for a method for fitting a lens. The method comprises obtaining an image of the lens. The method also comprises identifying an edge of a lens on an eye in the image. The method also comprises associating a number of zones with the image of the lens based on the edge of the lens. The method also comprises identifying the value for each zone in the number of zones based on intensities within the lens. The method also comprises designing a new lens based on the value to reach a desired value.

Another illustrative embodiment provides a computer program product. The computer program product comprises a computer usable medium having computer usable program code for designing a lens. The computer program product also comprises computer usable program code for obtaining an image of the lens. The computer program product also comprises computer usable program code for identifying an edge of a lens on an eye in the image. The computer program product also comprises computer usable program code for associating a number of zones with the image of the lens based on the edge of the lens. The computer program product also comprises computer usable program code for identifying a value for each zone in the number of zones based on intensities within the lens. The computer program product also comprises computer usable program code for designing a new lens based on the value to reach a desired value.

Yet another illustrative embodiment provides a data processing system. The data processing system comprises a bus, at least one processor coupled to the bus, and a computer usable medium coupled to the bus. The computer usable medium contains a set of instructions for designing a lens. The computer usable medium comprises instructions for obtaining an image of the lens. The computer usable medium also comprises instructions for identifying an edge of a lens on an eye in the image. The computer usable medium also comprises instructions for associating a number of zones with the image of the lens based on the edge of the lens. The computer usable medium also comprises instructions for identifying the value for each zone in the number of zones based on intensities within the lens. The computer usable medium also comprises instructions for designing a new lens based on the value to reach a desired value.

DETAILED DESCRIPTION OF THE INVENTION

Figure 1:
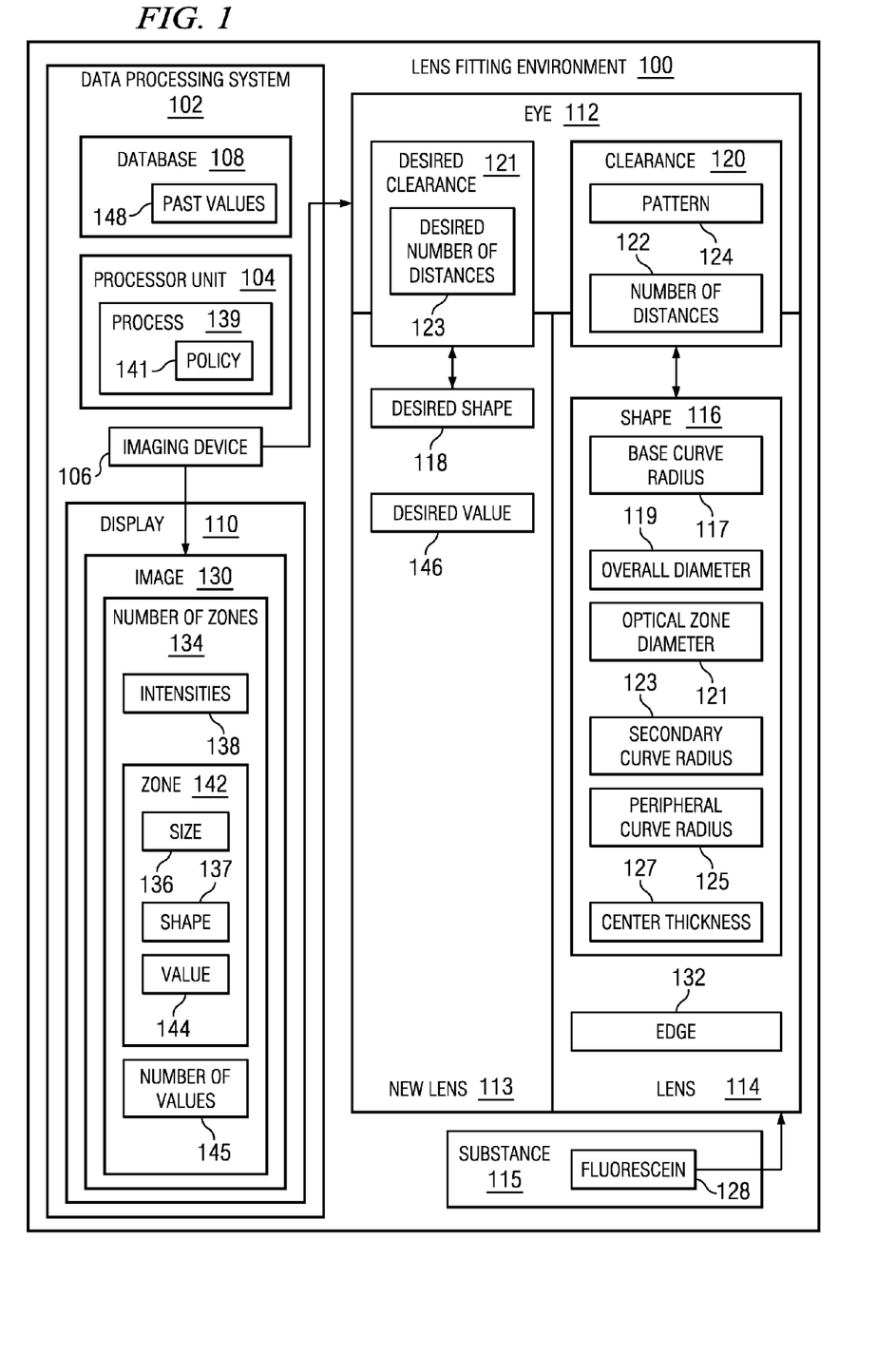
FIG. 1 is a block diagram of a contact lens fitting environment in accordance with an illustrative embodiment.

Turning to FIG. 1, an illustration of a block diagram of a contact lens fitting environment is depicted in accordance with an illustrative embodiment. Lens fitting environment 100 may be implemented using data processing system 200 in FIG. 2. Lens fitting environment 100 includes data processing system 102. Data processing system 102 is an example of one illustrative embodiment of data processing system 200 in FIG. 2.

In these illustrative embodiments, data processing system 102 includes hardware components such as processor unit 104, imaging device 106, database 108, and display 110. Processor unit 104 serves to execute instructions for software that may be loaded into memory. Processor unit 104 may be an example of one implementation of processor unit 204 in FIG. 2.

In these illustrative embodiments, lens fitting environment 100 may be an environment to fit a contact lens, such as lens 114. Lens fitting environment also includes eye 112, new lens 113, and substance 115. Eye 112 is the eye of a person being fitted for contact lenses, such as lens 114. In this illustrative example, lens 114 may correct vision, protect eye 112, be used for aesthetic purposes such as changing eye color, other purposes, or a combination thereof. In an illustrative example, lens 114 may be a rigid gas permeable lens. In different embodiments, lens 114 may be a soft contact lens. Lens 114 fits over eye 112.

Lens 114 has shape 116. Shape 116 is the shape of lens 114 and is described using base curve radius 117, overall diameter 119, optical zone diameter 121, secondary curve radius 123, peripheral curve radius 125, center thickness 127, and other measurements. Base curve radius 117 is the curvature of the back of lens 114. Overall diameter 119 is the diameter of lens 114 from the edges of lens 114. Optical zone diameter 121 is the diameter of the optic zone of lens 114. The optic zone is the central area or zone that provides optical correction for vision of a patient. The optic zone diameter varies depending on the pupil size of the patient, the overall diameter of lens 114, and peripheral curve width. Secondary curve radius 123 is the curve immediately surrounding the optic zone. Peripheral curve radius 125 is the radius of additional curves on the back surface of lens 114 that surround the optic zone to help adjust the fit of lens 114 to a patient. Peripheral curves allow the back surface of lens 114 to follow the gradual sloping of the cornea which is steeper in the center and flattens towards the periphery. Peripheral curves have a width and radius of curvature. The peripheral curve is the outermost curve. Center thickness 127 is the thickness of the center of lens 114. The different curves and measurements may form shape 116 of lens 114 and is described in more detail in FIG. 3.

Shape 116 of lens 114 may not be desired shape 118. Shape 116 has clearance 120. Clearance 120 provides number of distances 122 between a number of points along eye 112 and a number of corresponding points along lens 114. Desired shape 118 has desired clearance 121. Desired clearance 121 provides desired number of distances 123 between a number of points along eye 112 and a number of corresponding points along new lens 113.

Substance 115 is used to identify clearance 120. Substance 115 may be any substance which can be used to identify clearance 120. In these illustrative embodiments, substance 115 may be fluorescein 128. In these examples, fluorescein 128 is applied in the form of dye drops to eye 112 of the person. Fluorescein 128 indicates clearance 120 between different points between eye 112 and lens 114 at number of distances 122. Fluorescein 128 may be a bright orange dye that fluoresces lime green in the presence of cobalt blue light. The greater the concentration of fluorescein 128 that accumulates at different number of distances 122 in clearance 120, the brighter and more intense the light becomes at those different number of distances 122. The greater each distance of number of distances 122, the more fluorescein may accumulate at that distance.

In these illustrative embodiments, imaging device 106 is connected to processor unit 104. Examples of imaging device 106 may include a digital camera and other devices useful for measuring and/or obtaining image 130 of lens 114 on eye 112. The illustrative embodiments are not limited to the specific technique used to obtain image 130. Nevertheless, the illustrative embodiments use such devices to obtain image 130 of lens 114 on eye 112 for the purposes of lens fitting.

Image 130 may be shown on display 110. Display 110 is a hardware device such as a liquid crystal display, or other type of display device. Processor unit 104 may identify the position of lens 114 on eye 112 using edge detection software to identify edge 132 of lens 114. Once the position of lens 114 has been identified, processor unit 104 may identify number of zones 134 on image 130 over lens 114.

Number of zones 134 may be of any shape or size of at least one pixel 136 of image 130. Number of zones 134 indicates areas and pixels where intensities 138 of fluorescein 128 will be identified. In an illustrative embodiment, a person fitting lens 114 may identify number of zones 134. In different illustrative embodiments, processor unit 104 may identify number of zones 134 according to policy 141 using process 139. Policy 141 comprises rules which are configured to identify number of zones 134 in order to identify intensities 138 useful in designing new lens 113.

Each zone 142 in number of zones 134 has size 136, shape 137, and value 144. Size 136 may be any size of at least one pixel on image 130. Shape 137 may be any shape, such as, for example, rectangle, square, circle, arc, line, non-symmetrical shape, or any other shape. Value 144 is an indication of intensities 138 for zone 142. Value 144 may be identified for zone 142, a pixel of zone 142, or a group of pixels for zone 142. Value 144 may be a numerical value. Value 144 for shape 137 may show pattern 124 of clearance 120. For example, value 144 may show that the apex of lens 114 on eye 112 has a greater clearance 120 than edge 132 of lens 114 or vice versa. In other examples, value 144 may show other patterns as well.

A person fitting lens 114 may use value 144 along with number of values 145 to design new lens 113. Value 144 may indicate that measurements of lens 114 may be changed, such as measurements of base curve radius 117, overall diameter 119, optical zone diameter 121, secondary curve radius 123, peripheral curve radius 125, center thickness 127, and other measurements. The changes to the measurements of lens 114 may result in desired value 146 for new lens 113. In different illustrative embodiments, processor unit 104 may identify changes of measurements of lens 114 desirable to design new lens 113. Processor unit 104 may identify changes using past values 148 stored in database 108. Past values 148 may be values of past fittings. Database 108 may be stored on a storage device such as persistent storage 208 in FIG. 2. The database contains measurements of one or more eyes that were measured with respect to the techniques described herein. Preferably, the database contains the measurements of many different eyes. The database can then be used to create fitting sets of rigid gas permeable lenses, or to create template designs for rigid gas permeable lenses based on a pattern 124 of intensities 138 indicated by value 144.

In different illustrative embodiments, a person fitting lens 114 may examine lens 114 after fluorescein 128 has been applied. The person fitting lens 114 may identify pattern 124 separately from processor unit 104.

The illustration of lens fitting environment 100 in FIG. 1 is not meant to imply physical or architectural limitations to the manner in which different advantageous embodiments may be implemented. Other components in addition to and/or in place of the ones illustrated may be used. Some components may be unnecessary in some advantageous embodiments. Also, the blocks are presented to illustrate some functional components. One or more of these blocks may be combined and/or divided into different blocks when implemented in different advantageous embodiments.

For example, in some advantageous embodiments, information for lens 114 and eye 112 may also be stored in database 108. In different advantageous embodiments, instead of past values 148 being used to design new lens 113, absolute measurements may be given by processor unit 104 when identifying intensities 138.

Figure 2:
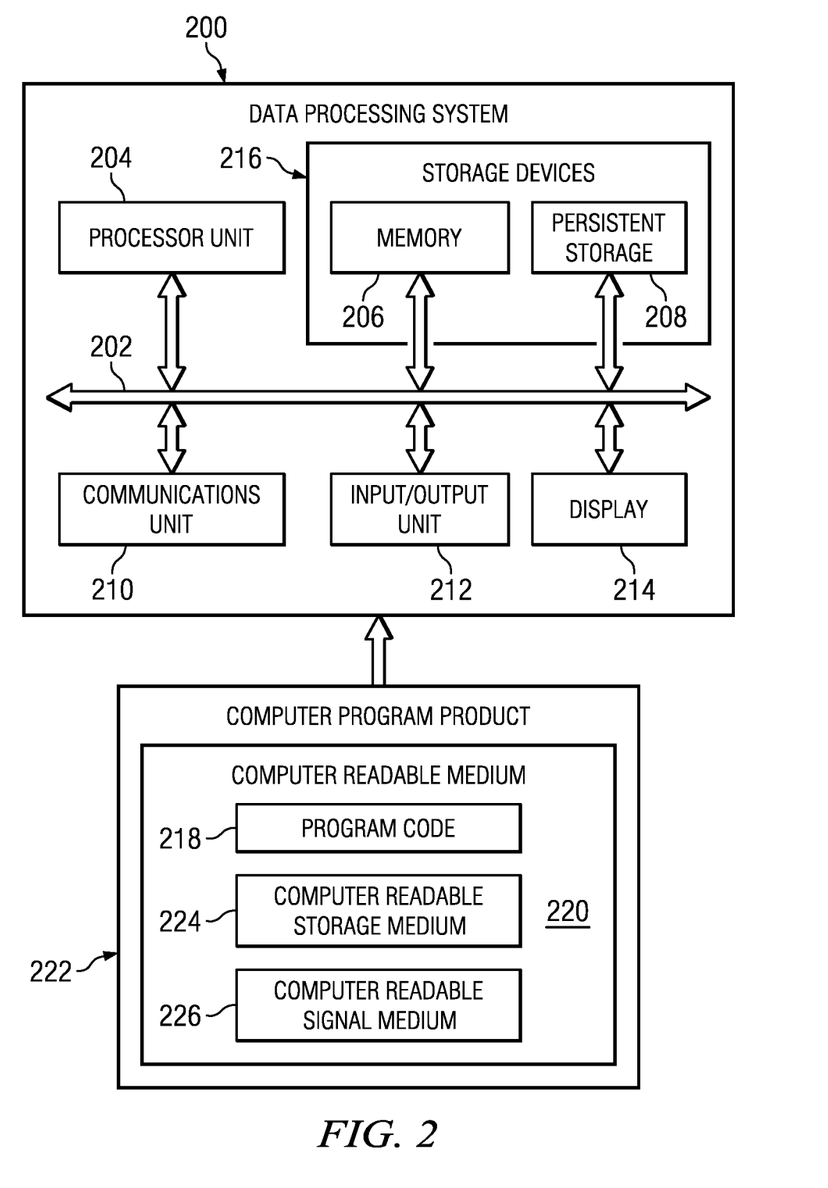
FIG. 2 is a diagram of a data processing system, in accordance with an illustrative embodiment.

Turning now to FIG. 2, an illustration of a data processing system is depicted in accordance with an illustrative embodiment. Data processing system 200 is an example of one implementation for data processing system 102 in FIG. 1. In this illustrative example, data processing system 200 includes communications fabric 202, which provides communications between processor unit 204, memory 206, persistent storage 208, communications unit 210, input/output (I/O) unit 212, and display 214.

Processor unit 204 serves to execute instructions for software that may be loaded into memory 206. Processor unit 204 may be a number of processors, a multi-processor core, or some other type of processor, depending on the particular implementation. A number, as used herein with reference to an item, means one or more items. Further, processor unit 204 may be implemented using a number of heterogeneous processor systems in which a main processor is present with secondary processors on a single chip. As another illustrative example, processor unit 204 may be a symmetric multi-processor system containing multiple processors of the same type.

Memory 206 and persistent storage 208 are examples of storage devices 216. A storage device is any piece of hardware that is capable of storing information, such as, for example, without limitation, data, program code in functional form, and/or other suitable information either on a temporary basis and/or a permanent basis. Memory 206, in these examples, may be, for example, a random access memory or any other suitable volatile or non-volatile storage device. Persistent storage 208 may take various forms, depending on the particular implementation.

For example, persistent storage 208 may contain one or more components or devices. For example, persistent storage 208 may be a hard drive, a flash memory, a rewritable optical disk, a rewritable magnetic tape, or some combination of the above. The media used by persistent storage 208 also may be removable. For example, a removable hard drive may be used for persistent storage 208.

Communications unit 210, in these examples, provides for communications with other data processing systems or devices. In these examples, communications unit 210 is a network interface card. Communications unit 210 may provide communications through the use of either or both physical and wireless communications links.

Input/output unit 212 allows for input and output of data with other devices that may be connected to data processing system 200. For example, input/output unit 212 may provide a connection for user input through a keyboard, a mouse, and/or some other suitable input device. Further, input/output unit 212 may send output to a printer. Display 214 provides a mechanism to display information to a user.

Instructions for the operating system, applications, and/or programs may be located in storage devices 216, which are in communication with processor unit 204 through communications fabric 202. In these illustrative examples, the instructions are in a functional form on persistent storage 208. These instructions may be loaded into memory 206 for processing by processor unit 204. The processes of the different embodiments may be performed by processor unit 204 using computer implemented instructions, which may be located in a memory, such as memory 206.

These instructions are referred to as program code, computer-usable program code, or computer-readable program code that may be read and processed by a processor in processor unit 204. The program code in the different embodiments may be embodied on different physical or computer readable storage medium, such as memory 206 or persistent storage 208.

Program code 218 is located in a functional form on computer readable medium 220 that is selectively removable and may be loaded onto or transferred to data processing system 200 for processing by processor unit 204. Program code 218 and computer readable medium 220 form computer program product 222 in these examples. In one example, computer readable medium 220 may be computer readable storage medium 224 or computer readable signal medium 226. Computer readable storage medium 224 may include, for example, an optical or magnetic disk that is inserted or placed into a drive or other device that is part of persistent storage 208 for transfer onto a storage device, such as a hard drive, that is part of persistent storage 208. Computer readable storage medium 224 also may take the form of a persistent storage, such as a hard drive, a thumb drive, or a flash memory, that is connected to data processing system 200. In some instances, computer readable storage medium 224 may not be removable from data processing system 200. In these illustrative examples, computer readable storage medium 224 is a non-transitory computer readable storage medium.

Alternatively, program code 218 may be transferred to data processing system 200 using computer readable signal medium 226. Computer readable signal medium 226 may be, for example, a propagated data signal containing program code 218. For example, computer readable signal medium 226 may be an electromagnetic signal, an optical signal, and/or any other suitable type of signal. These signals may be transmitted over communication links, such as wireless communication links, optical fiber cable, coaxial cable, a wire, and/or any other suitable type of communications link. In other words, the communications link and/or the connection may be physical or wireless in the illustrative examples.

The different components illustrated for data processing system 200 are not meant to provide architectural limitations to the manner in which different embodiments may be implemented. The different illustrative embodiments may be implemented in a data processing system including components in addition to, or in place of, those illustrated for data processing system 200. Other components shown in FIG. 2 can be varied from the illustrative examples shown. The different embodiments may be implemented using any hardware device or system capable of running program code.

As another example, a storage device in data processing system 200 is any hardware apparatus that may store data. Memory 206, persistent storage 208, and computer readable medium 220 are examples of storage devices in a tangible form.

In another example, a bus system may be used to implement communications fabric 202 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 206, or a cache, such as found in an interface and memory controller hub that may be present in communications fabric 202.

The different illustrative embodiments recognize and take into account that lens fitting by visual inspection may result in inaccurate changes in a new lens design. Additionally, when the correct changes are not made, more fittings may take place. The extra fittings result in extra time and money.

The different illustrative embodiments provide a method, computer system, and computer program product to fit a lens. The method comprises obtaining an image of the lens. The method also comprises identifying an edge of a lens on an eye in the image. The method also comprises associating a number of zones with the image of the lens based on the edge of the lens. The method also comprises identifying the value for each zone in the number of zones based on intensities within the lens. The method also comprises designing a new lens based on the value to reach a desired value.

Figure 3:
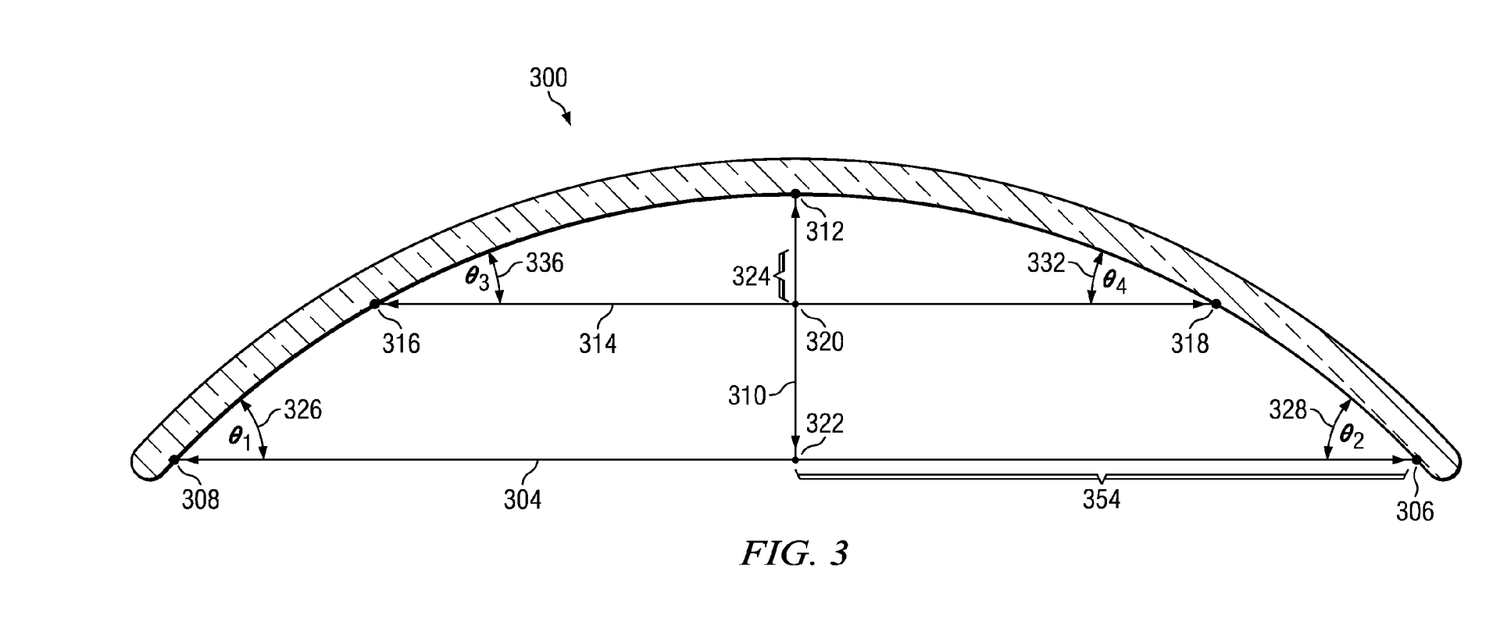
FIG. 3 is an illustration of a cross section image of a lens in accordance with an illustrative embodiment.

Turning to FIG. 3, an illustration of a cross section image of a lens is depicted in accordance with an illustrative embodiment. Cross section image 300 in FIG. 3 may be an example of one illustrative embodiment of lens 114 in FIG. 1. Cross section image 300 is a cross section image of a lens, in accordance with an illustrative embodiment.

Cross section image 300 can be measured using a digital imaging device connected to a computer, such as data processing system 200 in FIG. 2. Examples of digital imaging devices include an ultrasound device, an optical coherence tomography device, and a Scheimpflug camera system, and other devices useful for measuring an eye. The illustrative embodiments are not limited to the specific technique used to produce cross section image 300. Nevertheless, the illustrative embodiments use such devices to derive the shape of the lens. In particular, a shape of the lens is derived using the sagittal image. The shape is converted to a curvature of a lens. The curvature is designed such that the lens, once manufactured, can be worn over a surface of the eye.

The shape of the lens can be derived from cross section image 300 using different methods. In one illustrative embodiment, a first line, or chord 304 is drawn at first point 306 on the surface of the lens to second point 308 on the surface of the lens. Second point 308 is opposite the first point 306 relative to cross section image 300.

Sagittal line 310 is then drawn from chord 304 to apex 312. Sagittal line 310 can be considered a second line from the chord 304 to apex 312. As can be seen, sagittal line 310 is perpendicular to chord 304. The distances of these lines are then measured. From these distances, a curvature of the lens at first point 306 and second point 308 can be determined.

In this illustrative embodiment, apex 312 is located at the center of the cornea of the eye when the lens is worn. However, apex 312 can be located at any point on the lens along the cornea of the eye and is not limited to the center.

Mathematically, a radius of curvature of the lens at first point 306 and second point 308 is defined by a formula defined by:

$$z = y^2 / [r_0 + \sqrt{(r_o^2 - py^2)}]$$

wherein z is the length of sagittal line 310 (the second line), y is a length of chord 304 (first chord) divided by two, $r_0$ is the radius of curvature of the lens at first point 306 and second point 308, and p is a first asphericity of the eye at the first point 306 and second point 308. The shape of the lens can be characterized by the radius of curvature, which can be characterized as a first radius of curvature.

Additionally, multiple chords can be drawn parallel to chord 304 and perpendicular to sagittal line 310. At each chord, a different curvature of the lens at the corresponding two points can be determined. In this way, many different curvatures of the lens can be determined at multiple cross sections of the lens. These different curvatures can be combined to determine an overall shape of the lens. The more chords are measured, and the closer the chords are together, the more accurate the derived shape of the lens.

Thus, for example, the above method of deriving a shape of the lens can include drawing second chord 314 from third point 316 on the surface of the lens to fourth point 318 on the surface of the lens, wherein third point 316 is opposite fourth point 318 relative to the image, and wherein second chord 314 intersects sagittal line 310 at fifth point 320, which is different than sixth point 322 of the intersection of first chord 304 and sagittal line 310. A second radius of curvature of the lens at third point 316 and fourth point 318 is defined by a second mathematical formula defined by:

$$z_1 = y_1^2 / [r_1 + \sqrt{(r_1^2 - p_1 y_1^2)}]$$

wherein $z_1$ comprises third length 324 of sagittal line 310 measured between apex 312 and fifth point 320, $y_1$ comprises a fourth length of second chord 314 divided by two, $r_1$ is the second radius of curvature, and $p_1$ is a second asphericity of the lens at third point 316 and fourth point 318. The shape of the lens is derived by combining the first radius of curvature and the second radius of curvature.

In an illustrative embodiment, the first chord comprises a first meridian and the second chord comprises a second meridian. In this case, measuring the lens further includes identifying a principle meridian of the lens and scanning the lens at the principle meridian to determine a third radius of curvature of the lens at the principle meridian. Scanning can be performed using corneal topography. The shape of the lens can be further derived using both the first radius of curvature and the third radius of curvature.

In an illustrative embodiment, the shape of the lens can also be determined using angles measured between corresponding chords and corresponding lines tangential to the lens at corresponding points of intersection of the chords at the edge of the eye. Still further, the shape of the lens can be further refined by combining a shape derived using these angles and a shape derived using the techniques described above with respect to sagittal line 310. For example, angle $\theta_1$ 326 is the angle between chord 304 and a line tangential to the lens at second point 308. Similarly, angle $\theta_2$ 328 is the angle between chord 304 and a line tangential to the lens at first point 306. Likewise, angle $\theta_3$ 336 is the angle between second chord 314 and a line tangential to the lens at third point 316 and angle $\theta_4$ 332 is the angle between second chord 314 and a line tangential to the lens at fourth point 318. Using these angles, a shape of the lens can be determined using a method of best fit spheres.

The process of determining the shape of the lens can be improved through the use of edge detection software. Specifically, the process described above with respect to FIG. 3 can be automated using edge detection software. Use of edge detection software is a faster method to measure the sagittal depth at specified points. Additionally, edge detection software can be used with respect to more complex shapes than the arcs shown in FIG. 3. An "arc," as used in this application, is a chord section, such as chord section 354. An example of a more complex arc would be a chord section that is drawn, with respect to sagittal line 310 at an angle other than ninety degrees.

Figure 4:
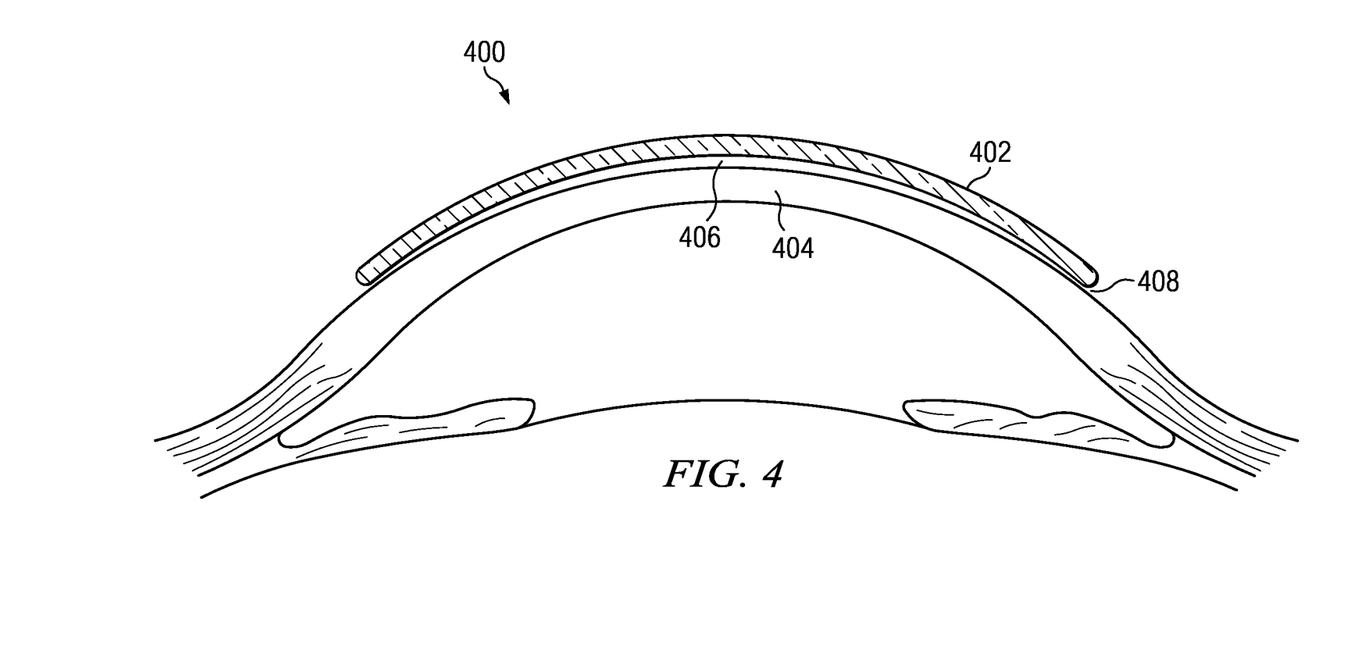
FIG. 4 is an illustration of a cross section image of an eye fitted with a contact lens in accordance with an illustrative embodiment.

Turning to FIG. 4, an illustration of a cross section image of an eye fitted with a lens is depicted in accordance with an illustrative embodiment. Cross section image 400 is the same as cross section image 300 of FIG. 3; however, lens 402 has been placed over the eye. Lens 402 may be an example of one implementation of lens 114 in FIG. 1.

Lens 402 rests over cornea 404. Cornea 404 may be an example of one implementation of eye 112 in FIG. 1. Between lens 402 and cornea 404 is clearance 406. Clearance 406 may be different for different points along cornea 404 between cornea 404 and lens 402. Clearance 406 may be an example of one implementation of clearance 120 in FIG. 1.

Clearance 406 may be where a substance, such as fluorescein accumulates. In this particular embodiment, more fluorescein may accumulate at clearance 406 than clearance 408. Accordingly, a value of the intensity of a zone applied to clearance 406 may be different from a value of the intensity of a zone applied to clearance 408. In different embodiments, a zone may include both clearance 406 and clearance 408. If a zone has more than one pixel, a value may be identified for the group of pixels or a different value may be identified for each pixel in the zone.

Figure 5:
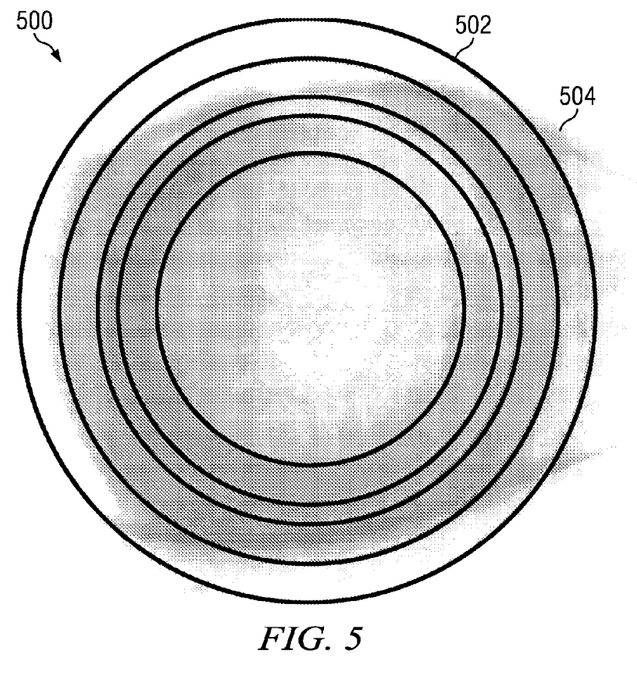
FIG. 5 is an illustration of an image of an eye with a number of zones in accordance with an illustrative embodiment.

Turning to FIG. 5, an illustration of an image of an eye with a number of zones is depicted in accordance with an illustrative embodiment. Image 500 may be an example of one implementation of image 130 in FIG. 1. Image 500 includes zones 502 and fluorescein 504.

Zones 502 are in the shape of circles. Zones 502 may be an example of one implementation of number of zones 134 in FIG. 1. Values for each zone of zones 502 may be taken at each pixel in image 500 or for a group of pixels. The value will correspond to the intensity of the brightness of fluorescein 504 obtained by an imaging device. The distance between the circles may be any distance. Past values such as past values 148 in FIG. 1 may indicate a desired distance. Fluorescein 504 indicates clearance between the lens and the eye.

Image 500 shows a pupil of the eye. Since the pupil of the eye may be darker than the rest of the eye, the intensity of the fluorescein may be different from other areas of the image for more reasons than just the clearance of the lens from the eye. In different illustrative embodiments, the change in contrast from the pupil to other points of the eye may be compensated for by adjusting the values obtained from the image.

Figure 6:
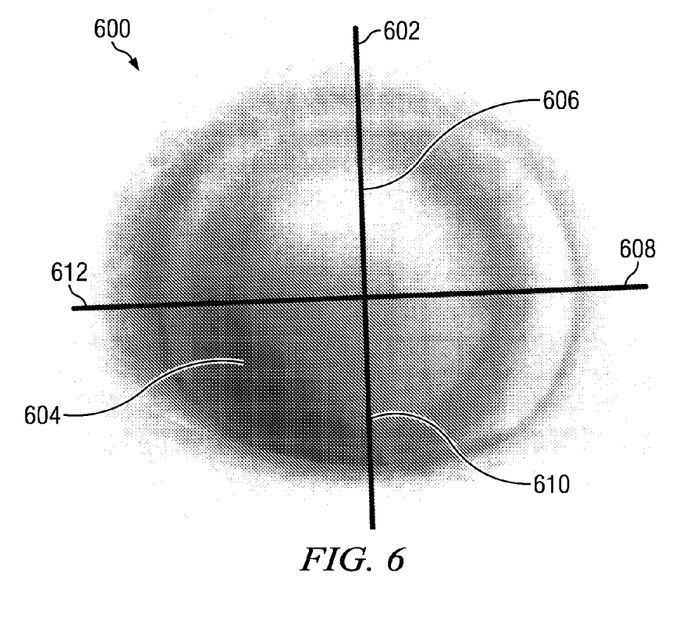
FIG. 6 is an illustration of an image of an eye with a number of zones in accordance with an illustrative embodiment.

Turning to FIG. 6, an illustration of an image of an eye with a number of zones is depicted in accordance with an illustrative embodiment. Image 600 may be an example of one implementation of image 130 in FIG. 1. Image 600 includes zones 602 and fluorescein 604.

Zones 602 may be an example of one implementation of number of zones 134 in FIG. 1. Values for each zone of zones 602 may be taken at each pixel in image 600 or for a group of pixels. The value will correspond to the intensity of the brightness of fluorescein 604 obtained by an imaging device. The position of each line may be different in different illustrative embodiments. Furthermore, more lines may be used in different illustrative embodiments. Past values such as past values 148 in FIG. 1 may indicate a desired distance. Fluorescein 604 indicates clearance between the lens and the eye.

In this illustrative example, zones 602 include zones 606, 608, 610, and 612. The four zones together make a cross pattern. Each zone 606, 608, 610, and 612 will be used to identify values corresponding to intensities of fluorescein for the pixels located within each zone 606, 608, 610, and 612. In other examples, other numbers of zones may be present. For example, in some implementations, 3 zones, 5 zones, or 8 zones may be used. The number of zones may be selected by a user or data processing system, such as data processing system 200 in FIG. 2. The size, shape, and number of zones may be based on past sessions of fittings. For example, zones may be placed in areas that were corrected in a previous fitting session.

Figure 7:
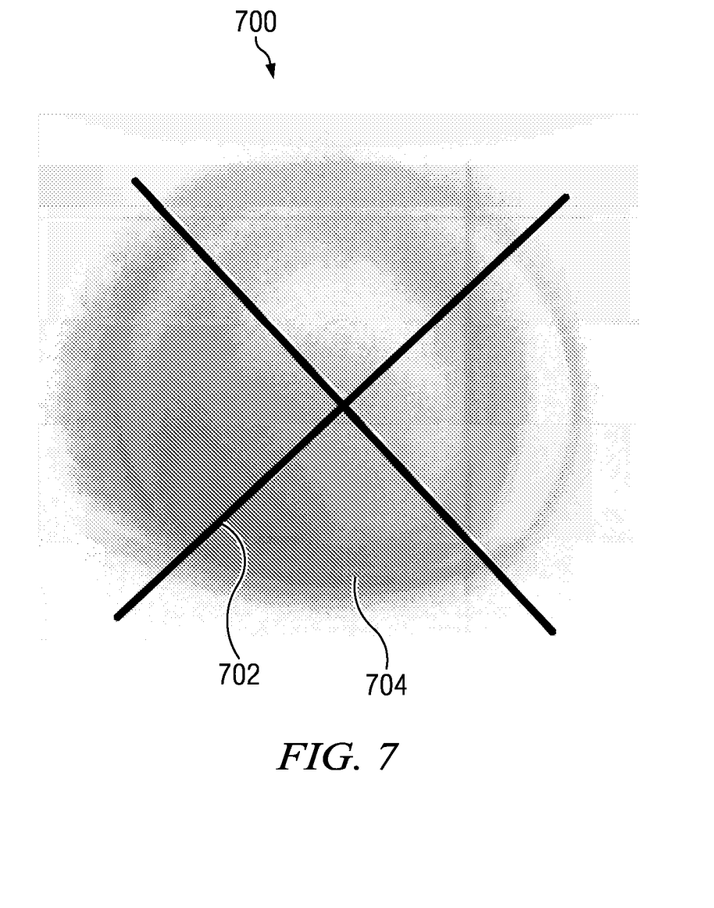
FIG. 7 is an illustration of an image of an eye with a number of zones in accordance with an illustrative embodiment.

Turning to FIG. 7, an illustration of an image of an eye with a number of zones is depicted in accordance with an illustrative embodiment. Image 700 may be an example of one implementation of image 130 in FIG. 1. Image 700 includes zones 702 and fluorescein 704.

Zones 702 are in straight lines in a crisscross pattern and diagonal pattern. Zones 702 may be an example of one implementation of number of zones 134 in FIG. 1. Values for each zone of zones 702 may be taken at each pixel in image 700 or for a group of pixels. The value will correspond to the intensity of the brightness of fluorescein 704 obtained by an imaging device. The position of each line may be different in different illustrative embodiments. Furthermore, more lines may be used in different illustrative embodiments. Past values such as past values 148 in FIG. 1 may indicate a desired distance. Fluorescein 704 indicates clearance between the lens and the eye.

Figure 8:
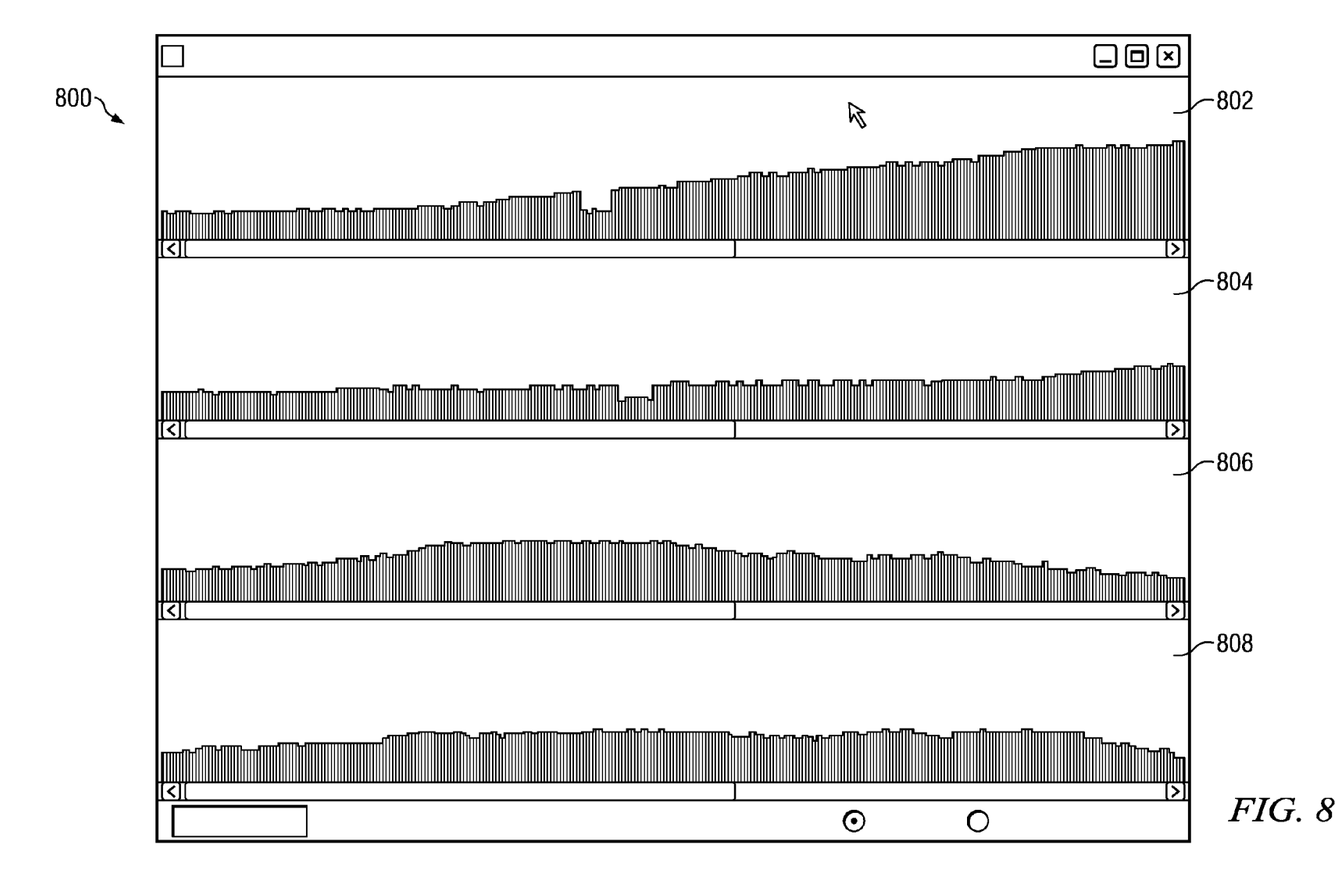
FIG. 8 is an illustration of a graph of values in accordance with an illustrative embodiment.

FIG. 8 is an illustration of a graph of values in accordance with an illustrative embodiment. Graph 800 can be implemented as, but not limited to a table of data, a flat file, an array, or a database. Graph 800 represents actual data taken of an eye using a digital imaging device according to the techniques described with respect to FIG. 1. This data can be used to create a lens, such as new lens 113 in FIG. 1. Graph 800 can be stored in a memory of a data processing system, such as memory 206 of FIG. 2, and subsequently processed using a data processing system, such as data processing system 200 of FIG. 2.

Graph 800 comprises four bar graphs 802, 804, 806, and 808. Each of bar graphs 802, 804, 806, and 808 corresponds to a different zone in an image, such as image 600 in FIG. 6. For example, bar graph 802 may correspond to zone 606, bar graph 804 may correspond to zone 608, bar graph 806 may correspond to zone 610, and bar graph 808 may correspond to zone 612, in FIG. 6. Each bar graph represents values for intensity levels of fluorescein in images such as image 600 in FIG. 6. Values from graph 800 may be used to design a new lens. Bar graphs 802 and 804 show a dip in the change in values at a rate that is inconsistent with the rest of the graphs. The dip may be an irregularity in the image, such as an air bubble.

Figure 9:
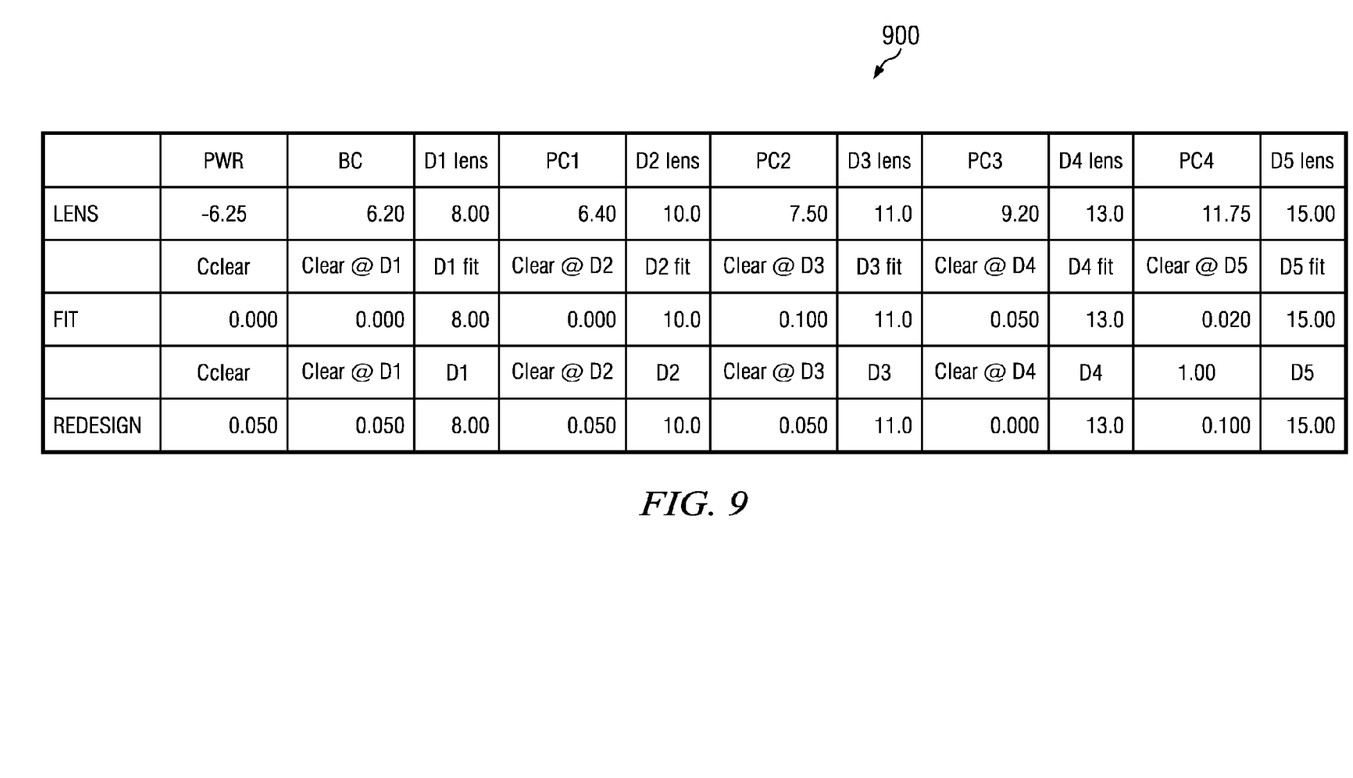
FIG. 9 is an illustration of a data structure usable to form a contact lens, wherein the data structure is generated using a data processing system in accordance with an illustrative embodiment.

FIG. 9 is an illustration of a data structure usable to form a lens, wherein the data structure is generated using a data processing system, in accordance with an illustrative embodiment. Data structure 900 can be implemented as, but not limited to a table of data, a flat file, an array, or a database. Data structure 900 represents actual data taken of an eye using a digital imaging device according to the techniques described with respect to FIG. 1. This data can be used to create a lens, such as new lens 113 in FIG. 1. Data structure 900 can be stored in a memory of a data processing system, such as memory 206 of FIG. 2, and subsequently processed using a data processing system, such as data processing system 200 of FIG. 2. The measurements in FIG. 9 are indicated in millimeters.

Data structure 900 can contain data for the central clearance (Cclear). The central clearance is the distance between the eye and the center of the lens. Data structure 900 can also contain data for refractive power (PWR). Refractive power represents the amount of refraction needed to give a patient 20/20 vision. A negative number indicates nearsightedness and a positive number indicates farsightedness. The larger the number, the more correction is applied.

Data structure 900 can also contain data for a base clearance (BC). The base clearance shows how much the lens should curve to match the back curvature of the cornea. Data structure 900 can also contain data for one or more peripheral clearances (PC). There can be different peripheral clearances for each measured diameter (D). For example, PC1 can be the peripheral clearance at diameter 1 (D1).

A user or processor unit may adjust the measurements in data structure 900 based on intensities of an image identified in lens fitting environment 100 in FIG. 1. Also, the measurements in data structure 900 may be used with the process in FIG. 11.

Data structure 900 can contain different peripheral clearances measurements. In different embodiments, data structure 900 may also contain other measurements such as, for example, overall diameter, optical zone diameter, center thickness, and other measurements.

Figure 10:
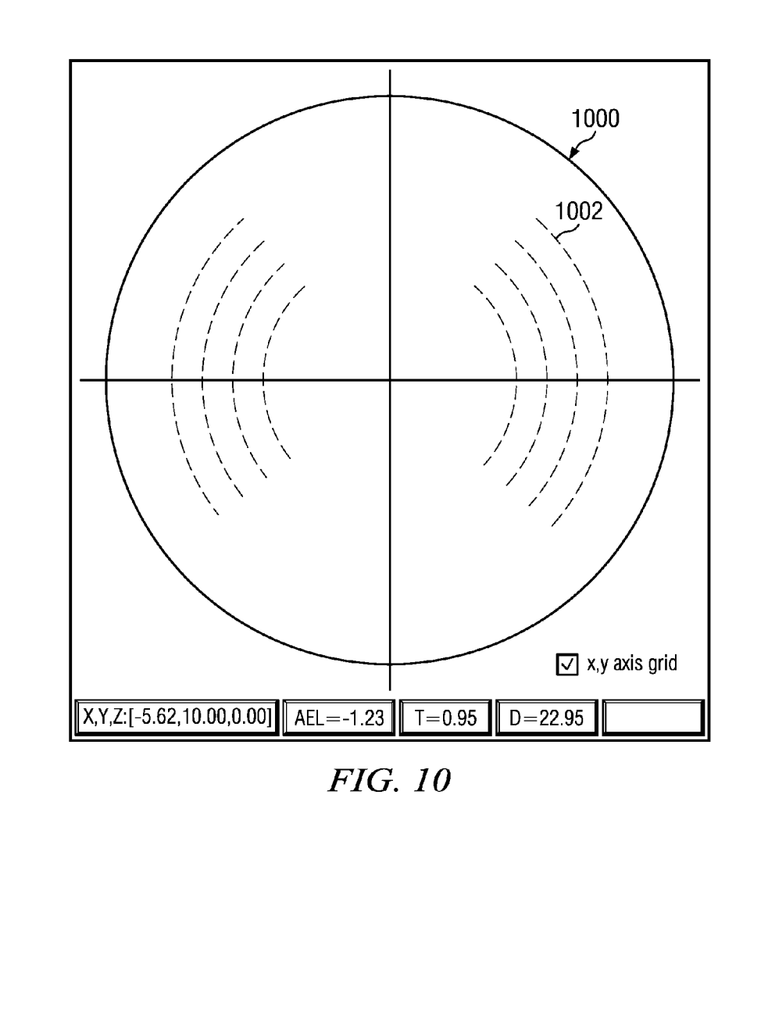
FIG. 10 is an illustration of a lens with markings in accordance with an illustrative embodiment.

Turning to FIG. 10, an illustration of a lens with markings is depicted in accordance with an illustrative embodiment. Lens 1000 may be an example of one illustration of lens 114 in FIG. 1. Lens 1000 may be etched with markings 1002. Markings 1002 may be etched on lens 1000 during manufacturing. Markings 1002 may correspond to zones, such as zones 502 in FIG. 5.

Figure 11:
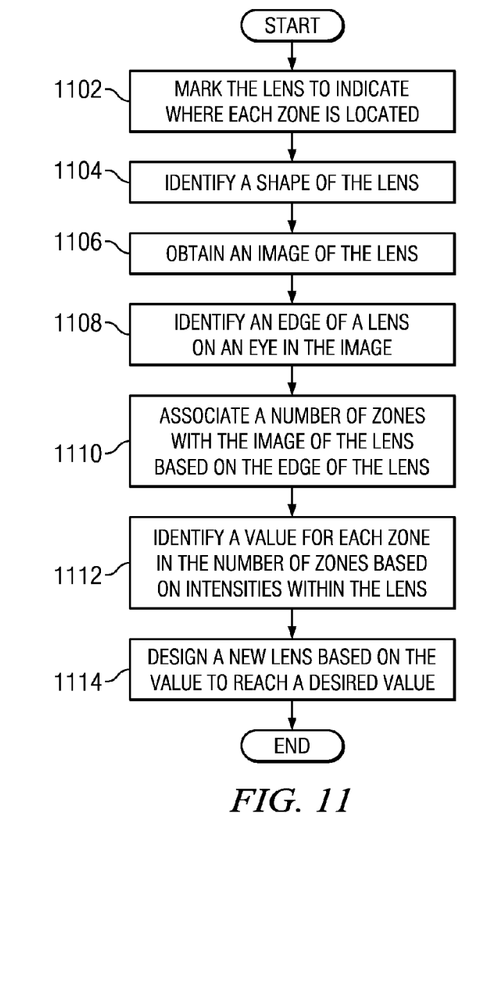
FIG. 11 is an illustration of a flowchart of a process for fitting a lens in accordance with an illustrative embodiment.

FIG. 11 is an illustration of a flowchart of a process for manufacturing a lens, in accordance with an illustrative embodiment. The process described in FIG. 11 can be implemented using software acting on the data, such as the data in data structure 900 of FIG. 9. Such data can be generated according to the techniques described with respect to FIG. 1. The computer can be any data processing system, such as data processing system 200 of FIG. 2. Together, the imaging device, the software, the data, and the computer form a system that implements the process. The result of this process is a lens manufactured according to the techniques described with respect to FIG. 1.

The process begins by marking the lens to indicate where each zone is located (step 1102). The markings on the lens may indicate where the zones are to be positioned. The markings may indicate the peripheral clearance to be used as zones. Each zone may be at least one pixel on the image. In an illustrative embodiment, the digital imaging device may identify and apply zones based on the physical marking on the lens. The process then identifies a shape of the lens (step 1104). The shape may be identified using a digital imaging device or the shape may be known from manufacturing data. The shape of the lens is identified to allow more accurate changes in measurement. The process obtains an image of the lens (step 1106). A digital imaging device may obtain the image. The image may include the lens, fluorescein, and eye.

The process then identifies an edge of a lens on an eye in the image (step 1108). The edge may be identified through edge detection software. Identifying the edge of a lens helps to identify the location of the lens. The process then associates a number of zones with the image of the lens based on the edge of the lens (step 1110). A processor unit may create the number of zones by executing software. The process may implement a policy for identifying the number of zones, the size of the number of zones, and the shape of the number of zones. A user, such as a doctor, may also identify the number of zones, the size of the number of zones, and the shape of the number of zones. The processor and/or user may place the number of zones over markings on the lens. Identifying the number of zones may include identifying the number of the number of zones and the placement of the number of zones.

The policy comprises a set of rules for identifying the number of zones, the size of the number of zones, and the shape of the number of zones. For example, the set of rules may identify the number of zones by using a fixed number of zones within the edge of the lens. In different illustrative embodiments, the number of zones may be as many zones that can fit given each zone is a fixed distance apart from each other. The policy may have a set of rules that identify the number of zones in different manners.

The process identifies a value for each zone in the number of zones based on intensities within the lens (step 1112). Step 1112 may comprise identifying the value for each zone based on a brightness of a substance located between the lens and an eye, wherein the brightness is greater as the distance is greater. The brightness may correspond to the amount of substance in each zone. The substance may be fluorescein. The process then designs a new lens based on the value to reach a desired value (step 1114). Thereafter, the process terminates.

Although the illustrative embodiments have been described with respect to manufacturing rigid gas permeable lenses, the illustrative embodiments are not limited to this type of lens. The illustrative embodiments can be used to create any kind of custom lens.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The different illustrative embodiments provide a method, computer system, and computer program product to fit contacts. The method comprises obtaining an image of the lens. The method also comprises identifying an edge of a lens on an eye in the image. The method also comprises associating a number of zones with the image of the lens based on the edge of the lens. The method also comprises identifying the value for each zone in the number of zones based on intensities within the lens. The method also comprises designing a new lens based on the value to reach a desired value.

The illustrative embodiments provide a way to decrease the amount of time and number of fittings needed to fit a rigid gas permeable lens on a patient. The fluorescein dye used to identify clearances and changes to the lens are performed by a computer system and imaging device. The illustrative embodiments provide for a more objective method of identifying fluorescein patterns.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention can take the form of an entirely hardware embodiment, an entirely software embodiment or an embodiment containing both hardware and software elements. In a preferred embodiment, the invention is implemented in software, which includes but is not limited to firmware, resident software, microcode, etc.

Furthermore, the invention can take the form of a computer program product accessible from a computer-usable or computer-readable medium providing program code for use by or in connection with a computer or any instruction execution system. For the purposes of this description, a computer-usable or computer readable medium can be any tangible apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modems, and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated.

What is claimed is:

1. A method for fitting a lens, the method comprising:
   obtaining an image of the lens with an imaging device;
   identifying an edge of the lens on an eye in the image;
   implementing a policy in a processor for identifying a number of zones, a size of the number of zones, and a shape of the number of zones in the lens, each zone in the number of zones defined by physical markings on the lens;
   marking the lens with the physical markings to indicate a location of each zone in the number of zones, the physical markings including a cross pattern;
   identifying and applying the plurality of zones with a digital imaging device based on the physical markings on the lens;
   associating the number of zones with the image of the lens based on the edge of the lens;
   identifying a value for each zone in the number of zones based on a brightness of a substance located between the lens and the eye, wherein the brightness is greater as the distance is greater between the lens and the eye, and wherein the brightness corresponds to an amount of substance in each zone;
   generating a graph to indicate the intensities substantially at each location in the cross pattern zone; and
   designing a new lens based on the value in each zone to reach a desired value in each zone.

2. The method of claim 1, further comprising:
   generating a data structure that includes at least central clearance, refractive power, and base clearance for the lens; and
   determining a shape of the new lens based on the data structure.

3. The method of claim 1, wherein the substance is fluorescein.

4. The method of claim 1 further comprising:
comparing the value to the shape of the lens at the zone where the value was identified.

5. The method of claim 1 further comprising:
identifying a desired shape in the lens based on the value and past values stored in a database.

6. The method of claim 1 further comprising:
marking the lens to indicate where each zone is located;
preparing a set of data tables that include the values along a set of zones, the set of data tables indicating changes in spacing along each zone in the set of zones between the lens and the eye; and
using the data tables in designing the new lens.

7. A nontransitory computer program product comprising:
a computer usable medium having computer usable program code for designing a lens, the computer program product including:
computer usable program code for obtaining an image of the lens with an imaging device;
computer usable program code for identifying an edge of the lens on an eye in the image;
computer usable program code for implementing a policy in a processor for identifying a number of zones, a size of the number of zones, and a shape of the number of zones in the lens, each zone in the number of zones defined by physical markings on the lens;
computer usable program code for marking the lens with the physical markings to indicate a location of each zone in the number of zones, the physical markings including a cross pattern;
computer usable program code for identifying and applying the plurality of zones with a digital imaging device based on the markings on the lens;
computer usable program code for associating the number of zones with the image of the lens based on the edge of the lens;
computer usable program code for identifying a value for each zone in the number of zones based on a brightness of a substance located between the lens and the eye, wherein the brightness is greater as the distance is greater between the lens and the eye, and wherein the brightness corresponds to an amount of substance in each zone;
computer usable program code for generating a graph to indicate the intensities substantially at each location in the cross pattern zone; and
computer usable program code for designing a new lens based on the value in each zone to reach a desired value in each zone.

8. The computer program product of claim 7 further comprising:
computer usable program code for generating a data structure that includes at least central clearance, refractive power, and base clearance for the lens; and
computer usable program code for determining a shape of the new lens based on the data structure.

9. The computer program product of claim 7, wherein the substance is fluorescein.

10. The computer program product of claim 7 further comprising:
computer usable program code for comparing the value to the shape of the lens at the zone where the value was identified.

11. The computer program product of claim 7 further comprising:
computer usable program code for identifying a desired shape in the lens based on the value and past values stored in a database.

12. The computer program product of claim 7, further comprising:
computer usable program code for marking the lens to indicate where each zone is located;
computer usable program code for preparing a set of data tables that include the values along a set of zones, the set of data tables indicating changes in spacing along each zone in the set of zones between the lens and the eye; and
computer usable program code for using the data tables in designing the new lens.

13. A data processing system comprising:
a bus;
at least one processor coupled to the bus;
a computer usable medium coupled to the bus, wherein the computer usable medium contains a set of instructions for designing a lens;
instructions for obtaining an image of the lens by an imaging device;
instructions for identifying an edge of the lens on an eye in the image;
instructions for implementing a policy in a processor for identifying a number of zones, a size of the number of zones, and a shape of the number of zones in the lens, each zone in the number of zones defined by physical markings on the lens;
instructions for marking the lens with the physical markings to indicate a location of each zone in the number of zones, the physical markings including a cross pattern;
instructions for identifying and applying the plurality of zones with a digital imaging device based on the markings on the lens;
instructions for associating the number of zones with the image of the lens based on the edge of the lens;
instructions for identifying a value for each zone in the number of zones based on a brightness of a substance located between the lens and the eye, wherein the brightness is greater as the distance is greater between the lens and the eye, and wherein the brightness corresponds to an amount of substance in each zone;
instructions for generating a graph to indicate the intensities substantially at each location in the cross pattern zone; and
instructions for designing a new lens based on the value in each zone to reach a desired value in each zone.

14. The data processing system of claim 13, further comprising:
instructions for generating a data structure that includes at least central clearance, refractive power, and base clearance for the lens; and
instructions for determining a shape of the new lens based on the data structure.

15. The data processing system of claim 13, wherein the substance is fluorescein.

16. The data processing system of claim 13 further comprising:
instructions for comparing the value to the shape of the lens at the zone where the value was identified.

17. The data processing system of claim 13 further comprising:
instructions for identifying a desired shape in the lens based on the value and past values stored in a database.

18. The data processing system of claim 13, further comprising:

instructions for marking the lens to indicate where each zone is located;

instructions for preparing a set of data tables that include the values along a set of zones, the set of data tables indicating changes in spacing along each zone in the set of zones between the lens and the eye; and instructions for using the data tables in designing the new lens.

* * * * *